US006787131B2

(12) United States Patent
Lever et al.

(10) Patent No.: US 6,787,131 B2
(45) Date of Patent: Sep. 7, 2004

(54) METHOD FOR ENHANCING INTEGRITY OF EPITHELIUM USING RETINOIC ACID

(75) Inventors: Andrea M. Lever, Pittsford, NY (US); Richard V. Smerbeck, Pittsford, NY (US); O. William Lever, Jr., Pittsford, NY (US); Joseph C. Salamone, Boca Raton, FL (US)

(73) Assignee: Bausch & Lomb Incorporated, Rochester, NY (US)

( * ) Notice: Subject to any disclaimer, the term of this patent is extended or adjusted under 35 U.S.C. 154(b) by 196 days.

(21) Appl. No.: 10/023,351

(22) Filed: Dec. 17, 2001

(65) Prior Publication Data

US 2002/0115720 A1 Aug. 22, 2002

Related U.S. Application Data

(60) Provisional application No. 60/256,713, filed on Dec. 19, 2000.

(51) Int. Cl.$^7$ .............................. A61K 31/74; A61F 2/14
(52) U.S. Cl. ..................... 424/78.04; 424/427; 424/429
(58) Field of Search ............................... 424/78.04, 427, 424/429

(56) References Cited

U.S. PATENT DOCUMENTS

| 4,826,871 A | | 5/1989 | Gressel et al. ............... 514/438 |
| 5,032,392 A | | 7/1991 | Varma .......................... 424/78 |
| 6,136,850 A | * | 10/2000 | Park et al. .................. 514/458 |

FOREIGN PATENT DOCUMENTS

| EP | 0 473 159 A1 | * | 4/1992 |
| EP | 1 016 406 A1 | | 5/2000 |
| WO | WO 95/03784 | | 9/1995 |
| WO | WO 96/10403 | | 11/1996 |

* cited by examiner

Primary Examiner—Carlos A. Azpuru
(74) Attorney, Agent, or Firm—Rita D. Vacca; Denis A. Polyn; Robert B. Furr, Jr.

(57) ABSTRACT

A method for improving the integrity of the corneal epithelium by introducing into the eye an effective amount of a ophthalmically compatible retinoid sufficient to enhance the integrity of the corneal epithelium.

5 Claims, No Drawings

METHOD FOR ENHANCING INTEGRITY OF EPITHELIUM USING RETINOIC ACID

This application claims the benefit of provisional application No. 60/256,713, filed Dec. 19, 2000.

FIELD OF THE INVENTION

This invention relates to the prevention of damage to the cornea in mammals resulting from discontinuities in the epithelial layer.

BACKGROUND OF THE INVENTION

Ophthalmic lenses have been investigated for a number of years. Such materials can generally be subdivided into two major classes, namely hydrogels and non-hydrogels. Non-hydrogels do not absorb appreciable amounts of water, whereas hydrogels can absorb and retain water in an equilibrium state.

Those skilled in the art have long recognized that the surface characteristics of contact lenses play a major role in their ocular compatibility. For example, it is known that increasing the hydrophilicity of the contact lens surface improves the wettability of the contact lenses. This in turn is associated with improved wear comfort of contact lenses. Additionally, the surface of the lens can affect the lens's susceptibility to deposition, particularly the deposition of proteins and lipids from the tear fluid during lens wear. Accumulated deposits can cause eye discomfort or even inflammation. In the case of extended wear lenses (i.e. lenses used without daily removal of the lens before sleep), the surface is especially important, since extended wear lenses must be designed for high standards of comfort and biocompatibility over an extended period of time.

The degree of ocular compatibility is more specifically the compatibility of the superior corneal epithelium with the posterior surface of the contact lens. Because the radius of curvature of the posterior surface of the contact lens is usually slightly smaller than radius of curvature of the convex anterior surface of the cornmeal epithelium, the thinnest portion of the tear film separating the corneal epithelium and the contact lens is usually at the outer perimeter of the contact lens.

One can envision this area by striking an imaginary circle on the cornea that is concentric with the pupil and that has a radius equal to that of the contact lens. Allowing for the normal movement of the contact lens on the cornea, one would broaden the width of the imaginary circle. This circle or its arcuate portions are then of principal interest in the present invention.

Since the introduction of soft daily wear contact lenses in the late 1960's and extended wear soft contact lenses in the 1980's, the number of people wearing contact lenses for vision correction has increased dramatically. It is estimated that the number of contact lenses wears in the United States alone is in excess of 25 million[1]. Contact lenses are prescribed by optometrists and ophthalmologists, and most contact lens wearers follow their health care provider's instructions on the use and care of the contact lenses. Thus the vast majority of contact lens wearers enjoy the benefits of their contact lenses with no adverse side effects.

Although the relative numbers of problems arising from contact lens wear are quite small, the absolute number of incidents has risen with the increasing number of contact lens wearers. Thus the increasing popularity of contact lenses has yielded a concomitant increase in the incidence of complications related to contact lens wear. Corneal infiltrates and superior epithelial arcuate lesions (SEALs) are of particular interest since neither are completely described with respect to either causative factors or predisposing conditions. The SEALs appear principally in arcuate sections of the circular region defined by the outer posterior edge of the contact lens as discussed above.

Corneal infiltrates account for a small percentage of all contact lens-related problems and are more commonly found in extended wear versus daily wear patients. Corneal infiltrates arise in the cornmeal epithelium and are characterized by an inflammatory response, such that there is a visible (1 to 2 mm) accumulation of polymorphonucleocytes (PMNs) to the localized area. Infiltrates have been observed to be sterile and non-sterile, symptomatic and asymptomatic. Corneal infiltrates are most commonly found on the superior cornea, although are also found elsewhere. Most patients present with a single infiltrate, however multiple infiltrates are not uncommon. Generally, there is minimal disruption to the overlying epithelium and epithelial edema or superficial punctate keratitis is found in approximately half of the cases. Anterior chamber inflammation is absent or minimal in affected patients. A number of causative agents have been proposed, ranging from hypersensitivity/toxicity to contact lens care product preservatives[2], to bacteria[3]/blepharitis[4], to protein lens deposits[5]. However, given the range and degree of symptoms it seems most probable that these infiltrates are more likely the result of a general immunological response, since PMNs are relatively non-specific components of the immune system, which respond to a variety of chemotactic and other signals.

Superior epithelial arcuate lesions are primarily the result of mechanical damage of the corneal epithelium, typically due to contact lens wear. Characteristic arcuate epithelial staining is observed where micro-abrasions readily take up fluorescein at the site of the arc of contact between the edge of the lens and the cornea.

The similarity between these two conditions, aside from contact lens wear, is the involvement or proximity to the corneal epithelium. Thus it would be desirable to provide a method of preventing these conditions or mitigating their severity.

SUMMARY OF THE INVENTION

The invention provides a method for improving the integrity of the corneal epithelium in an eye wearing a contact lens comprising introducing an ophthalmically compatible form of a retinoid into the eye in an amount sufficient to enhance the integrity of the corneal epithelium. The method of the invention may optionally include examining for the presence of retinoid deficiency (clinical and sub-clinical). Suitable methods for determining the level of available retinoic acids include measuring the level of retinoic acids in the serum or tear film.

DETAILED DESCRIPTION

In accordance with the invention, it has been found that certain individuals in the contact lens wearing population may be predisposed to developing superior epithelial arcuate lesions and/or corneal infiltrates. While not to limit the scope of the invention by a recitation of theory, it is believed that insufficient levels of retinoid (alone or in combination with other factors) or other nutritional deficiencies may increase the surface roughness of the epithelium. This increased surface roughness can be accompanied by local retinoid deficiencies. When the roughness of the epithelium increases, it may minimally cause the epithelium to become "leaky" or functionally ineffective at completely protecting the underlying layers of the corneal epithelium. As a result of the lack of cellular differentiation, the epithelium is more susceptible to invasion by microorganisms and/or to chemotactic substances, which can recruit the leukocytes observed in non-sterile and sterile infiltrates alike. Exposure of the underlying epithelial layers to chemotactic substances and microbial invaders/metabolites will cause the accumulation of PMNs or other leukocytes characteristic of the corneal infiltrate phenomenon.

In addition (again, not to limit the invention by a recitation of theory) it is believed that insufficient levels of retinoid (alone or in combination with other factors) or other nutritional deficiencies which can result in local retinoid deficiencies, minimally cause the epithelium to be more susceptible or prone to SEALs. It has been found that the epithelium appears to be less resistant to mechanical abrasion due to the reduction of cellular differentiation as a direct result of retinoid deficiency.

Retinoids are known to have a profound influence on many aspects of ocular health. Vitamin A deficiency is well documented as a cause of childhood blindness, xerophthalmia, throughout the world. Sub-clinical vitamin A deficiency, without overt symptoms, has been observed in populations throughout the world[6,7,8,9]. Additionally, Vitamin A deficiency, clinical and sub-clinical is positively correlated with smoking. Vitamin A is known to regulate the proliferation and differentiation of corneal epithelial cells and to preserve the integrity of the conjunctiva, and thus has a significant impact on overall ocular health.

The effects of overt retinoid deficiency are obvious, with xerophthalmia being the most prominent outcome of severe deficiency causing half a million or more cases of pediatric blindness worldwide. However sub-clinical retinoid deficiencies, protein deficiencies (leading to decreased levels of retinol binding protein) and the long term effects of reversed early childhood and infant deficiencies are not well understood or characterized. Sub-clinical retinoid deficiencies are known to increase the severity of infectious morbidity, exacerbate iron deficient anemia, retard growth and are responsible for one to three million childhood deaths each year[10].

Vitamin A deficiency has also been shown to increase inflammatory responses. Vitamin A deficient rats exhibited 43% increased in the number of circulating leukocytes, had a four time higher T-cell proliferative response and a two times higher interferon-gamma production in vitro as compared to control animals. Granulocyte dependent inflammation was increased, the spontaneous release of nitric oxide form the peritoneal phagocytes was five time higher and the number of peritoneal mast cell was 1.5 times higher in vitamin A deficient animals in contrast to control animals[11]. Dawson, et al. evaluated the effect of marginal vitamin A status on the number and function of natural killer cells in aging Lewis rats. They determined that the cells lytic activity declined with increasing age and decreasing vitamin A supplementation, suggesting that in humans elderly people consuming diets chronically low in vitamin A may be at increased risk for infectious or neoplastic diseases[12].

Vitamin A is known to have a positive effect on epithelial integrity and cellular differentiation. Alterations in the epithelial lining of vital organs occur early in deficiency, suggesting an important role for the barrier function. Conjunctival-impression cytology testing can detect the presence of larger irregular keratinized cells and the absence of mucous-secreting goblet cells in vitamin A deficient individuals[13]. Increases in epithelial cellular stratification and keratinization can lead to decreases in barrier efficacy and subsequent increases in chemotactic substance and microorganism penetration into the epithelium. This is postulated to lead directly to an increase in corneal infiltrate occurrence, accounting for both sterile and non-sterile infiltrates, in affected individuals, as well as the appearance of SEALs due to vulnerable epithelium. Low plasma retinol levels have been shown to be correlated with low retinol binding protein plasma levels (r=0.77) indicating that, while vitamin A deficiency exists in malnourished populations, low retinol levels may be partly related to decreased levels of its carrier protein[14,15]. Additionally, decreased cellular differentiation and lower goblet cell densities directly impact the amount of mucin-like glycoprotein[16] and mucin produced[17]. Aside from contributing to both the rheology and stability of tear film, mucins also function as a physical barrier and bind microorganisms and immune cells specifically and non-specifically. Therefore, decreases in the production of these substances should also be related to an increase in corneal infiltrate occurrence in vitamin A deficient (or protein deficient) contact lens wearing individuals. Local or systemic vitamin A deficiency (resulting from diet or tobacco use) and protein malnutrition may have a significant influence on the occurrence of both corneal infiltrates and SEALs.

In accordance with the present invention, the retinoid may be administered topically or systemically. If the retinoid is administered locally, it is preferred to administer the retinoid in an ophthalmically compatible solution in the form of a drop.

The retinoid of the invention may be administered dropwise in an ophthalmic solution, or as a mist, gel or ointment. The method of the invention is useful for improving the long-term ophthalmic compatibility of extended wear contact lenses. In a preferred embodiment, the extended-wear contact lenses are silicone hydrogel lenses and the solution is administered dropwise or in the form of a contact lens conditioning solution.

Gels and ointments are particularly preferred for patients wearing rigid gas permeable (RGP) contact lenses, especially continuous-wear RGP lenses and orthokeratology lenses. When used in conjunction with orthokeratology lenses, the retinoid is administered as a gel or ointment to the eye before inserting the orthokeratology lens before sleep at night.

The retinoid may be administered as a coating on a contact lens. For example, the retinoid may be added to a lens care product such as a multipurpose cleaning and disinfecting solution. One example of multipurpose lens care solution is ReNu MultiPlus™ solution produced by Bausch & Lomb, Incorporated of Rochester, N.Y.

The retinoid may also be applied to the contact lens during the contact lens manufacturing process. The contact lens surface may be treated with a retinoid by any suitable means, for example: spreading, dipping or spraying. The mechanism by which the retinoid attaches to the surface of the contact lens is not critical for this invention provided that the retinoid can detach or desorb from the contact lens surface into the epithelium. One example of a useful attachment mechanism to achieve sustained release is covalent bonding between a contact lens surface and a retinol group. Alternatively, the retinoid may be attached to a polymer having both hydrophobic and/or hydrophilic sites. For example, the hydroxyl group of vitamin A palmitate can be attached to a dimethacrylate/glycidyl methacrylate (DMA/GMA) copolymer, which may then be attached to the surface of a contact lens through residual glycidyl groups. In a preferred embodiment, the retinoid is applied to the contact lens in a sustained release form, where, for example, a covalently bound retinoid is hydrolyzed from the lens thus liberating the free retinoid. Alternatively, hydrophobic interactions can be used to bind a hydrophobic retinod, such as vitamin A plamitate, to hydrophobic contact lens material. The vitamin A plamitate would be released from the contact lens in a controlled, sustained manner.

The retinoid may also be administered systemically, i.e., orally or by injection, to provide a normal level of retinoid in the serum. While normal levels of retinoids in the serum are physiologically beneficial, it has been found that such levels do not necessarily take the place of the method of the invention for treating SEALs and corneal infiltrates. For example, protein deficiency has been found to inhibit delivery of systemically administered retinoids to the epithelium. Thus it has surprisingly been found that the method of the invention is effective for treating and/or preventing recurrence of SEALs and corneal infiltrates even when serum retinoid levels would predict that no additional retinoid is needed.

The retinoid is administered in a vehicle within a range of suitable concentrations. At a minimum, the concentration of retinoid is sufficient to improve the integrity of the corneal epithelium. For an ophthalmic solution applied dropwise two to eight times per day, a suitable range of concentrations is from about 200 to about 5000 IU/ml, with the maximum concentration and dosage consistent with ocular comfort. One suitable treatment regimen for an ophthalmic solution containing vitamin A palmitate at a concentration of 1000 IU/ml is one or two drops per eye administered four times per day.

The contact lenses useful in the present invention may comprise rigid materials as well as soft (hydrogel) materials. Hydrogels comprise hydrated, crosslinked polymeric systems containing water in an equilibrium state. Conventional hydrogel lens materials include polymers containing monomers such as 2-hydroxyethyl methacrylate (HEMA), glyceryl methacrylate, N-vinylpyrrolidone (NVP) and N,N-dimethacrylamide.

Flexible ophthalmic lens materials useful in the present invention include silicone hydrogels as well as conventional hydrogels and low-water elastomeric materials. Examples of flexible ophthalmic lens materials useful in the present invention are taught in U.S. Pat. Nos. 5,908,906 to Künzler et al.; 5,714,557 to Künzler et al.; 5,710,302 to Künzler et al.; 5,708,094 to Lai et al.; 5,616,757 to Bambury et al.; 5,610,252 to Bambury et al.; 5,512,205 to Lai; 5,449,729 to Lai; 5,387,662 to Künzler et al. and 5,310,779 to Lai; which patents are incorporated by reference as if set forth at length herein.

U.S. Pat. Nos. 6,037,328, 6,008,317, 5,981,675, 5,981,669, 5,969,076, 5,945,465, 5,914,355, 5,858,937, 5,824,719 and 5,726,733 teach ophthalmic lens materials containing HEMA monomers.

U.S. Pat. Nos. 6,071,439, 5,824,719, 5,726,733, 5,708,094, 5,610,204, 5,298,533, 5,270,418, 5,236,969 and 5,006,622 teach ophthalmic lens materials containing glyceryl methacrylate monomers.

U.S. Pat. Nos. 6,008,317, 5,969,076, 5,908,906, 5,824,719, 5,726,733, 5,714,557, 5,710,302, 5,708,094, 5,648,515 and 5,639,908 teach ophthalmic lens materials containing NVP monomers.

U.S. Pat. Nos. 5,539,016, 5,512,205, 5,449,729, 5,387,662, 5,321,108 and 5,310,779 teach ophthalmic lens materials containing dimethacrylamide monomers.

The preferred conventional hydrogel materials typically contain HEMA, NVP and TBE (4-t-butyl-2-hydroxycyclohexyl methacrylate). Polymacom™ materials, for example the Soflens 66™ brand contact lenses (commercially available from Bausch & Lomb Incorporated of Rochester, N.Y.) are examples of particularly preferred conventional hydrogel materials.

Silicone hydrogels generally have a water content greater than about five weight percent and more commonly between about ten to about eighty weight percent. Materials are usually prepared by polymerizing a mixture containing at least one silicone-containing monomer and at least one hydrophilic monomer. Either the silicone-containing monomer or the hydrophilic monomer may function as a crosslinking agent (a crosslinker being defined as a monomer having multiple polymerizable functionalities) or a separate crosslinker may be employed. Applicable silicone-containing monomeric units for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995.

A preferred silicone hydrogel material comprises (in the bulk monomer mixture that is copolymerized) 5 to 50 percent, preferably 10 to 25, by weight of one or more silicone macromonomers, 5 to 75 percent, preferably 30 to 60 percent, by weight of one or more polysiloxanylalkyl (meth)acrylic monomers, and 10 to 50 percent, preferably 20 to 40 percent, by weight of a hydrophilic monomer. In general, the silicone macromonomer is a poly (organosiloxane) capped with an unsaturated group at two or more ends of the molecule. In addition to the end groups in the above structural formulas, U.S. Pat. No. 4,153,641 to Deichert et al. discloses additional unsaturated groups, including acryloxy or methacryloxy. Fumarate-containing materials such as those taught in U.S. Pat. Nos. 5,512,205, 5,449,729, and 5,310,779 to Lai are also useful substrates in accordance with the invention. Preferably, the siliconene macromonomer is a silicon-containing vinyl carbonate or vinyl carbamate or a polyurethane-polysiloxane having one or more hard-soft-hard blocks and end-capped with a hydrophilic monomer.

The suitable monomers that form hydrogels useful in the present invention include, for example, acids such as acrylic and methacrylic acid, amides such as N,N-dimethyl acrylamide, N,N-dimethyl methacrylamide, cyclic lactams such as N-vinyl-2-pyrrolidone and poly(alkene glycol)s functionalized with polymerizable groups. Examples of useful functionalized poly(alkene glycol)s include poly (diethylene glycol)s of varying chain length containing monomethacrylate or dimethacrylate end caps. In a preferred embodiment, the poly(alkene glycol) polymer contains at least two alkene glycol monomeric units. Still further examples are the hydrophilic vinyl carbonate or vinyl carbamate monomers disclosed in U.S. Pat. Nos. 5,070,215, and the hydrophilic oxazolone monomers disclosed in U.S. Pat. No. 4,910,277. Other suitable hydrophilic monomers will be apparent to one skilled in the art. In a particularly preferred embodiment, the hydrophilic monomers used in the contact lens material are capable of forming a stable complex with a cationic polysaccharide.

Rigid ophthalmic lens materials include rigid-gas-permeable ("RGP") materials. RGP materials typically comprise a hydrophobic crosslinked polymer system containing less than 5 wt. % water. RGP materials useful in accordance with the present invention include those materials taught in U.S. Pat. Nos. 4,826,936 to Ellis; 4,463,149 to Ellis; 4,604,479 to Ellis; 4,686,267 to Ellis et al.; 4,826,936 to Ellis; 4,996,275 to Ellis et al.; 5,032,658 to Baron et al.; 5,070,215 to Bambury et al.; 5,177,165 to Valint et al.; 5,177,168 to Baron et al.; 5,219,965 to Valint et al.; 5,336,797 to McGee and Valint; 5,358,995 to Lai et al.; 5,364,918 to Valint et al.; 5,610,252 to Bambury et al.; 5,708,094 to Lai et al.; and 5,981,669 to Valint et al. U.S. Pat. No. 5,346,976 to Ellis et al. teaches a preferred method of making an RGP material. The patents mentioned above are incorporated by reference as if set forth at length herein.

EXAMPLE

An ophthalmic ointment is formulated for treating SEALs and/or corneal infiltrates in accordance with the invention.

| INGREDIENT | CONCENTRATION |
|---|---|
| Retinoic Acid, USP | 0.05 mg/g |
| Mineral Oil, USP (67 centistokes) | 100 mg/g |
| White Petrolatum, USP | 899.9 mg/g |

The sterile ophthalmic ointment formulated as shown above is applied to the eyes in the form of a thin coating three or four times per day.

[1] Barr, J. T. 1997. Contact lenses and vision: the annual report. Contact Lens Spectrum. 12:21.
[2] Mondino, B. J. and L. R. Groden. 1980. Conjunctival hypermia and corneal infiltrates with chemically disinfected soft contact lenses. Arch. Ophthalmol. 98:1767.
[3] Friedlaender, M. H. 1979. Ocular and immunology. J. Allergy Clin Immunol. 63:51.
[4] Suchecki, J. K. , Ehlers, W. H., and P. C. Donshik. 1996. Peripheral corneal infiltrates associated with contact lens wear. CLAO J. 22:41.
[5] Suchecki, J. K. , Ehlers, W. H., and P. C. Donshik. 1996. Peripheral corneal infiltrates associated with contact lens wear. CLAO J. 22:41.
[6] Ahmed, F. 1999. Vitamin A deficiency in Bangladesh: a review and recommendations for improvement. Public Health Nutr. 2:1.
[7] Florentino, R. F., C. C. Tanchoco, M. P. Rodriguez, A. J. Cruz, and W. L. Molano. 1996. Interaction among micronutrient deficiencies and undernutrition in the Philippines. Biomed. Environ Sci. 9:348.
[8] Rodriguez, A. G. Guam'an, and D. P. Nelson. 1996. Vitamin A status of children in five Ecuadorian provinces. Bull. Pan. Health Organ. 30:234.
[9] Rice, A. L., R. J. Stoltzfus, A. de Francisco, J. Chakraborty, C. L. Kjolhede and M. A. Wahed. 1999. Maternal vitamin A or beta-carotene supplementation in lactating bangladeshi women benefits mothers and infants but does not prevent subclinical dificiency. J. Nutr. 129:356.
[10] Sommer, A. 1998. Xerophthalmia and vitamin A status. Prog. Retin. Eye Res. 17:9.
[11] Wiedermann, U., X. J. Chen, L. Enerback, L. A. Hanson, H. Kahu, and U. I. Dahlgren. 1996. Vitamin A deficiency increasses inflammatory reponses. Scand. J. Immunol. 44:578.
[12] Dawson, H. D., N. Q. Li, K. L. DeCicco, J. A. Nibert, and A. C. Ross. 1999. Chronic marginal vitamin A stutus reduces natural killer cell number and function in aging Lewis rats. J. Nutr. 129:1510.
[13] McCullough, F. S., C. A. Northrop-Clewes and D. I. Thurnham. 1999. The effect of vitamin A on epithelial integrity. Proc. Nutr. Soc. 58:289.
[14] Goetghebuer, T. at al. 1996. Significance of very low retinol levels during severe protein-energy malnutrition. J. Trop. Pediatr. 42:158.
[15] Donnen, P. 1996. Vitamin AQ deficiency and protein-energy malnutrition in a sample of pre-school age children in the Kivu Province in Zaire. Eur. J. Clin. Nutr. 50:456.
[16] Watanabe, H. et. al.. 1997. Expression of a mucin-like glycoprotein produced by ocular surface epithelium in normal and keratinized cells. Am J. Ophthalmol. 124:751.
[17] Tei, M., S. J. Spurr-Michaud, A. S. Tisdale, and I. K. Gipson. 2000. Vitamin A deficiency alters the expression of mucin genes by the rat ocular surface epithelium. IOVS. 41:82.

The scope of this invention is not intended to be limited by the recitation set forth above, but only by the following claims.

What is claimed is:

1. A method for improving the integrity of the corneal epithelium in an eye having a contact lens comprising introducing an ophthalmically compatible form of a retinoid directly into the eye in an amount sufficient to enhance the integrity of the corneal epithelium.

2. The method of claim 1 further comprising introducing the retinoid into the eye in the form of drops.

3. The method of claim 1 further comprising introducing the retinoid into the eye by applying the retinoid to a contact lens and placing the contact lens in the eye.

4. The method of claim 3 wherein said applying step further comprises dipping the contact lens in a solution containing the retinoid.

5. The method of claim 1 further comprising placing in the eye a retinoid in a sustained release form.

* * * * *